United States Patent [19]

McCort et al.

[11] Patent Number: 5,378,847
[45] Date of Patent: Jan. 3, 1995

[54] PROCESS FOR THE PREPARATION OF 1,2,4-SUBSTITUTED IMIDAZOLES AND RELATED AMINOALKYLIMIDAZOLE DERIVATIVES

[75] Inventors: Gary McCort, Paris; Jean-Claude Pascal, Cachan, both of France

[73] Assignee: Syntex Pharmaceuticals, Ltd., Maidenhead, England

[21] Appl. No.: 171,594

[22] Filed: Dec. 21, 1993

Related U.S. Application Data

[62] Division of Ser. No. 46,002, Apr. 9, 1992, Pat. No. 5,296,609.

[51] Int. Cl.⁶ .................. C07D 233/56; C07D 233/64
[52] U.S. Cl. .................... 544/370; 546/210; 548/335.5
[58] Field of Search .......... 544/370; 546/210; 548/335.5

[56] References Cited

U.S. PATENT DOCUMENTS 4,829,065  5/1989  Pascal et al. .................. 514/255
5,043,447  8/1991  Pascal et al. .................. 544/370

FOREIGN PATENT DOCUMENTS 132867  6/1987  Japan .

OTHER PUBLICATIONS

Insertion Reactions of Diethylaluminum Derivatives, by T. Hirabayashi et al *J. Organometallic. Chem.* (1969), vol. 21, pp. 273–280.
Sur un Noveau Procede de Syntheses de Derives Imidazoliques, by Eloy et al., *Eur. J. Med. Chem—Chimica Therapeutica*, (1974), pp. 602–606.

*Primary Examiner*—Joseph Paul Brust
*Assistant Examiner*—Mary Susan H. Gabilan
*Attorney, Agent, or Firm*—Brian Lewis; David A. Lowin; Alan M. Krubiner

[57] ABSTRACT

The invention provides a new and efficient process for preparing 2,4(5)-substituted or 1,2,4-substituted imidazole derivatives.

The invention also provides a process for preparing substituted aminoalkylimidazole derivatives, useful for the treatment of mammals having a variety of disease states, including stroke, epilepsy, hypertension, angina, migraine, arrhythmia, thrombosis, embolism, and the like.

10 Claims, No Drawings

PROCESS FOR THE PREPARATION OF 1,2,4-SUBSTITUTED IMIDAZOLES AND RELATED AMINOALKYLIMIDAZOLE DERIVATIVES

This application is a division of application Ser. No. 08/046,002, filed Apr. 9, 1992, now U.S. Pat. No. 5,296,609.

BACKGROUND OF THE INVENTION

1. Field of the Invention

The invention relates to a process for the preparation of 1,2,4-substituted (and 2,4(5)-substituted) imidazole derivatives. The invention also relates to the use of such derivatives for a preferred preparation of substituted aminoalkylimidazole derivatives; examples of such compounds are disclosed in U.S. Pat. No. 4,829,065. The invention also relates to novel substituted aminoalkylimidazole derivatives, which are useful for treating ischaemia, particularly including disease states such as stroke.

2. Background to the Invention

Existing regioselective syntheses of 2,4(5)-substituted and 1,2,4-substituted imidazole derivatives of Formula (I) require several steps, are difficult to carry out, and give low overall yields; see, for example, *Comprehensive Heterocyclic Chemistry*, ed. A. R. Katritzky, Volume 5, page 457 (1984).

Processes for the preparation of compounds of Formula (II) where $-NR^6R^7$ represents a piperazine derivative are disclosed in U.S. Pat. Nos. 4,829,065 and 5,043,447. The '065 patent initially requires the preparation of an imidazole substituted at the 4(5)-position by $-CH_2OH$, followed by a two-step conversion to the desired product. The '447 patent discloses a more efficient process for the preparation of the desired substituted imidazolylalkylpiperazine derivatives, in that once the starting materials have been prepared, the process can be carried out in a single reaction vessel. However, the preparation of a potentially unstable iminoether hydrochloride is required initially, which is then converted to an amidine and reacted with a costly 1,2-dione to prepare the imidazole intermediate necessary for reaction with a substituted piperazine. Additionally, this process works poorly where the amidine is a benzamidine in which the phenyl possesses an electron withdrawing group.

The present process provides for an improved preparation of 2,4(5)-substituted and 1,2,4-substituted imidazole derivatives of Formula (I), and aminoalkylimidazole derivatives of Formula (II). The invention provides most particularly for a one-step process for the large-scale production of compounds of Formula (I), and a two-step process for the large-scale production of (II). These processes have surprising advantages over previously disclosed processes in that they do not require the use of potentially unstable imidoesters, iminoethers, chloroimidates, or the like, and the use of ammonia and concentrated hydrochloric acid is also avoided. Additionally, the intermediate compounds for the preparation of compounds of Formula (I) do not need to be isolated or purified during the process, and consequently the synthesis can be conducted in a single reaction vessel. Further, the compounds of Formula (I) can be prepared by cyclizing the alkynyl imine precursor in the absence of a catalyst, in which case compound (I) generally crystallizes out from the reaction mixture after the reaction is complete, in good yield and in high purity, such that there is no need for further purification. Alternatively, the compounds of Formula (I) can be prepared by cyclizing the alkynyl imine precursor in the presence of a catalyst, in which case the reaction time for completion of the reaction is considerably shortened.

Related Disclosures

Eloy et al. (*Eur. J. Med. Chem. Therapeutica* (1974), vol. 9, p 602-6) prepares 1,2,4-substituted imidazoles by reacting propargylamine with imidoesters, imidothioesters, amidines, or imidoyl chlorides.

Stoeck et al. (*Arch. Pharm.* (1976), Vol. 309, p 391-5 and 421-5) prepares 1,2,4-substituted imidazoles and oxazoles in low yield by reacting an imino ester with ammonia and an α-aminoketone (see also DE 2,533,211 to Schunock et al.).

P. N. Dhal et al. (*J. Just. Chem. Calcutta*, vol. 47, p 27-8) prepares 1,2,4-substituted imidazoles by reaction of an α,β-dione with an aldehyde and ammonia.

Bredereck et al. (*Newer methods of Preparative Organic Chemistry*, (1964), Vol. III, Academic Press, N.Y., p 241) prepares 1,2,4-substituted imidazoles by reaction of α-hydroxyketones or α-haloketones with a formamide.

SUMMARY OF THE INVENTION

In a first aspect, the present invention provides a process for the preparation of imidazole derivatives represented by the formula:

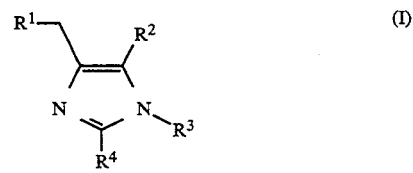

wherein:

$R^1$ is hydrogen, lower alkyl, or optionally substituted phenyl;

$R^2$ is hydrogen, lower alkyl, or optionally substituted lower alkyl phenyl;

$R^3$ is hydrogen, alkyl, optionally substituted phenyl, or optionally substituted biphenylmethyl;

$R^4$ is hydrogen, lower alkyl, optionally substituted phenyl, or $-SR^5$, in which $R^5$ is lower alkyl, optionally substituted phenyl, or optionally substituted benzyl;

and includes the step of cyclizing a compound represented by the formula:

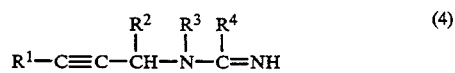

wherein $R^1$, $R^2$, $R^3$ and $R^4$ are as defined above, preferably in the presence of a palladium or gold catalyst.

A second aspect of the invention relates to the process for the preparation of compounds of Formula (4), and includes the step of reacting a compound represented by the formula:

$$R^1-C\equiv C-\overset{R^2}{\underset{|}{C}}H-\overset{R^3}{\underset{|}{N}}-Al\overset{R}{\underset{R}{\diagdown}} \quad (2)$$

wherein R is lower alkyl, and $R^1$, $R^2$ and $R^3$ are as defined above; with a compound of the formula $R^4CN$, followed by hydrolysis of the resulting aluminum complex.

A third aspect of the invention relates to the process for the preparation of compounds of Formula (2), and includes the step of reacting a compound represented by the formula:

$$R^1-C\equiv C-\overset{R^2}{\underset{|}{C}}H-NHR^3 \quad (1)$$

wherein $R^1$, $R^2$ and $R^3$ are as defined above; with a tri(lower alkyl)- or di(lower alkyl)halogeno- aluminum compound, preferably trimethylaluminum.

A fourth aspect of the invention relates to the process for the preparation of compounds represented by the formula:

(II)

wherein:
$R^1$ is hydrogen, or lower alkyl;
$R^3$ is hydrogen, or lower alkyl;
$R^4$ is lower alkyl, or optionally substituted phenyl;
$R^6$ is hydrogen, or lower alkyl;
$R^7$ is $$-X\overset{(CH_2)_mR^8}{\underset{R^9}{\diagdown}}$$

or $R^6$ and $R^7$ taken together with the nitrogen atom to which they are attached represent a group of the formula:

$$-N\overset{\diagup\diagdown}{\underset{\diagdown\diagup}{\phantom{x}}}Y-(CH_2)_n\overset{(CH_2)_mR^8}{\underset{R^9}{\diagdown}}$$

wherein:
m is 0 or 1;
n is 0, 1, 2 or 3;
$R^8$ is hydrogen, lower alkyl, or optionally substituted phenyl;
$R^9$ is optionally substituted phenyl;
X is $-(CH_2)_n-$, or 1-piperidin-4-yl; and
Y is $-CH-$, or $-N-$;
and includes the step of reacting a compound represented by the formula:

(I)

wherein $R^2$ is hydrogen, and $R^1$, $R^3$ and $R^4$ are as defined above with a compound represented by the formula:

$$H-N\overset{R^6}{\underset{R^7}{\diagdown}}$$

where $R^6$ and $R^7$ are as defined above; in the presence of formaldehyde.

A fifth aspect of the invention relates to compounds represented by the formula:

(II)

wherein:
$R^1$ is hydrogen, or lower alkyl;
$R^3$ is lower alkyl;
$R^4$ is lower alkyl, or optionally substituted phenyl;
$R^6$ is hydrogen, or lower alkyl;
$R^7$ is $$-X\overset{(CH_2)_mR^8}{\underset{R^9}{\diagdown}}$$

or $R^6$ and $R^7$ taken together with the nitrogen atom to which they are attached represent a group of the formula:

$$-N\overset{\diagup\diagdown}{\underset{\diagdown\diagup}{\phantom{x}}}Y-(CH_2)_n\overset{(CH_2)_mR^8}{\underset{R^9}{\diagdown}}$$

wherein:
m is 0 or 1;
n is 0, 1, 2 or 3;
$R^8$ is hydrogen, lower alkyl, or optionally substituted phenyl;
$R^9$ is optionally substituted phenyl;
X is $-(CH_2)_n-$, or 1-piperidin-4-yl; and
Y is $-CH-$, or $-N-$.

A sixth aspect of the invention relates to methods of treating mammals having a disease treated by direct neuronal protection or a disease treated by calcium channel inhibition, sodium channel inhibition, or inhibition of both calcium and sodium channels, including:

diseases treated by direct neuronal protection, such as ischaemia including focal and global ischaemia, cerebral ischaemia including ischaemia-induced neurodegeneration, perinatal asphyxia, spinal injuries, peripheral nerve ischaemia, peripheral nerve damage, head trauma, primary intracerebral hemorrhage, encephalopathy, epilepsy or epileptic psychotic symptoms, and neurological diseases such as Alzheimeres, Huntingtones chorea, Parkinsons and dementias; and diseases treated by calcium channel inhibition, sodium channel inhibition, or inhibition of both calcium and sodium channels, including:

diseases treated by inhibiting cerebrovascular vasospasm and by cerebrovascular vasodilation, such as migraine, stroke, vasospasm due to subarachnoid hemorrhage, and cerebrovascular ischaemia induced by cocaine abuse;

diseases treated by inhibiting cellular oedema, such as cerebral oedema and hyponatraemic encephalopathy;

cardiovascular diseases, such as hypertension, angina, stable and unstable angina, Prinzmetal angina, arrhythmia, thrombosis, myocardial infarction, embolism, and congestive heart failure such as chronic or acute cardiac failure;

diseases characterized by ischaemia of lower legs due to peripheral vascular disease, including intermittent claudication;

diseases characterized by spasms of smooth muscle, including reversible airways obstruction, asthma, spasms of the ureter, spasms of the bladder, uterine cramps, and irritable bowel syndrome;

prevention of vasoconstriction and/or ischaemic tissue damage during a surgical procedure, such as bypass grafts, angiography, angioplasty, organ preservation during transplant, hypertensive crisis, or post-operative hypertension;

diseases treated by diuresis; and uraemic encephalopathy, by administering to a mammal in need of such treatment a therapeutically effective amount of a compound of Formula (II), or a pharmaceutically acceptable salt thereof.

DETAILED DESCRIPTION OF THE INVENTION

Definitions

As used herein:

"Alkyl" means a branched or unbranched saturated hydrocarbon chain containing i to 12 carbon atoms, such as methyl, ethyl, propyl, tert-butyl, n-hexyl, n-octyl, n-decyl, and the like, unless otherwise indicated.

"Lower alkyl" means a branched or unbranched saturated hydrocarbon chain containing 1 to 6 carbon atoms, such as methyl, ethyl, propyl, isopropyl, tert-butyl, butyl, n-hexyl and the like, unless otherwise indicated.

"Lower alkoxy" means the group —O—R wherein R is lower alkyl is as defined above.

The term "halo" means fluoro, bromo, chloro or iodo, unless otherwise indicated.

The term "organoaluminum compound" means a tri(lower alkyl)aluminum or di(lower alkyl)-halogenoaluminum compound, for example trimethylaluminum, triethylaluminum, tri(n-propyl)aluminum, dimethylaluminum chloride, diethylaluminum chloride, and the like.

The terms "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform ("CHCl$_3$"), methylene chloride (or dichloromethane or "CH$_2$Cl$_2$"), diethyl ether, ethyl acetate, acetone, methylethyl ketone, methanol, ethanol, propanol, isopropanol, tert-butanol, dioxane, pyridine, and the like]. Unless specified to the contrary, the solvents used in the reactions of the present invention are inert solvents.

The compounds of Formula (II) form acid addition salts by virtue of the presence of basic nitrogen atoms. "Pharmaceutically acceptable salt" means a salt which retains the biological effectiveness and properties of the compounds of Formula (II), and which is not biologically or otherwise undesirable. Acid addition salts may be formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumetic acid, tartaric acid, citric acid, benzoic acid, cinnamic acid, mandelic acid, methanesulfonic acid, ethanesulfonic acid, p-toluenesulfonic acid, salicylic acid and the like.

"Optional" or "optionally" means that the subsequently described event or circumstance may or may not occur, and that the description includes instances where said event or circumstance occurs and instances in which it does not. For example, "optionally substituted phenyl" means that phenyl may or may not be substituted with a substituent selected from the group consisting of lower alkyl, lower alkoxy, nitro, hydroxy, trifluoromethyl and halo, and encompasses all possible isomeric phenyl radicals that are mono, di or trisubstituted. "Optionally substituted benzyl" means optionally substituted phenyl as defined above attached to a methylene group. "Optionally substituted biphenylmethyl" means that the biphenyl group may or may not be substituted with a substituent selected from the group consisting of lower alkyl, lower alkoxy, carboxy, tetrazole (including 1H-tetrazol-5-yl), nitro, hydroxy, trifluoromethyl and halo.

The compounds of Formula (II) may have one or more asymmetric centers (for example, where m is not 0, or where m is 0 and $R^8$ is lower alkyl) and can be produced as racemic mixtures or as individual stereoisomers. The individual stereoisomers may be obtained by resolving a racemic or non-racemic mixture of an intermediate at some appropriate stage of the synthesis, or by chiral synthesis of an appropriate intermediate, or by resolution of a compound of Formula (II). It is understood that the individual stereoisomers as well as racemic and non-racemic mixtures of stereoisomers are encompassed within the scope of the present invention.

The term "mammal" includes humans and all domestic and wild mammals, including, without limitation, cattle, horses, swine, sheep, goats, dogs, cats, rabbits, and the like.

The term "treatment" as used herein covers any treatment of a disease in a mammal, particularly a human, and includes:

(i) preventing the disease from occurring in a subject which may be predisposed to the disease but has not yet been diagnosed as having (ii) inhibiting the disease, i.e. arresting its development; or (iii) relieving the disease, i.e. causing regression of the disease.

The term "effective amount" means a dosage sufficient to provide treatment for the disease state being treated. This will vary depending on the patient, the disease and the treatment being effected.

The naming and numbering of the compounds of the present invention is illustrated below.

A compound of Formula (I) is numbered as follows:

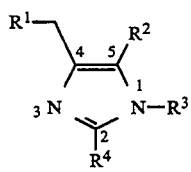

The compound of Formula (I) where $R^1$, $R^2$ and $R^3$ are hydrogen, and $R^4$ is 4-methylphenyl, is named 4(5)-methyl-2-(4-methylphenyl)-1H-imidazole.

The compound of Formula (I) where $R^1$ is methyl, $R^2$ is hydrogen, $R^3$ is n-butyl, and $R^4$ is 4-trifluoromethylphenyl, is named 1-(n-butyl)-4-ethyl-2-(4-trifluoromethylphenyl)imidazole.

The naming of compounds of Formula (II) varies according to the definition of —$NR^6R^7$. For example, where —$NR^6R^7$ represents a piperazine derivative, the compounds are named as such, and numbered as shown below:

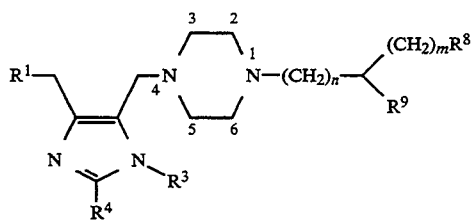

The compound of Formula (II) where m and n are 0, $R^1$ and $R^3$ are hydrogen, $R^4$ is 4-methylphenyl, and $R^8$ and $R^9$ are phenyl, is named: 1-diphenylmethyl-4-[(2-(4-methylphenyl)-4-methyl-1H-imidazol-5-yl)methyl]piperazine.

The compound of Formula (II) where m and n are 0, $R^1$ is hydrogen, $R^3$ is methyl, $R^4$ is 4-trifluoromethylphenyl, $R^8$ is hydrogen, and $R^9$ is 2,3,4-trimethoxyphenyl, is named 1-(2,3,4-trimethoxyphenyl)methyl-4-[(2-(4-trifluoro-methylphenyl)-1,4-dimethylimidazol-5-yl)methyl]piperazine.

Preferred Embodiments

In Step 1 of the process, the preferred aluminum compound is trimethylaluminum.

In Step 3 of the process, the cyclization is preferably carried out in the presence of a palladium or gold catalyst, more preferably a palladium(II) catalyst, most preferably palladium(II)acetate.

Among the family of compounds of the present invention, one preferred category includes the compounds of Formula (II) where $R^6$ and $R^7$ taken together with the nitrogen atom to which they are attached represent a group of the formula:

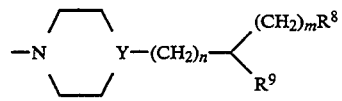

especially where m and n are 0. Within this preferred category, one preferred class includes those compounds where $R^1$ is hydrogen and Y is nitrogen. Within this class, one preferred group includes those compounds where $R^8$ and $R^9$ are both phenyl, especially where $R^3$ is methyl and $R^4$ is 4-trifluoromethylphenyl. A second preferred group includes those compounds where $R^8$ is hydrogen and $R^9$ is 2,3,4-trimethoxyphenyl, especially where $R^3$ is methyl and $R^4$ is 4-trifluoromethylphenyl.

METHODS OF PREPARATION

Preparation of Starting Materials

The starting compounds of Formula (1) are commercially available, or may be prepared by means well known in the art. Organoaluminum compounds, for example trimethylaluminum, are commercially available, for example from Aldrich Chemical Company.

Unless specified to the contrary, the preparations are carried out under an inert atmosphere, for example nitrogen or argon.

PROCESS FOR THE PREPARATION OF COMPOUNDS OF FORMULA (I)

The process for the preparation of compounds of Formula (I) is shown below in Reaction Scheme I:

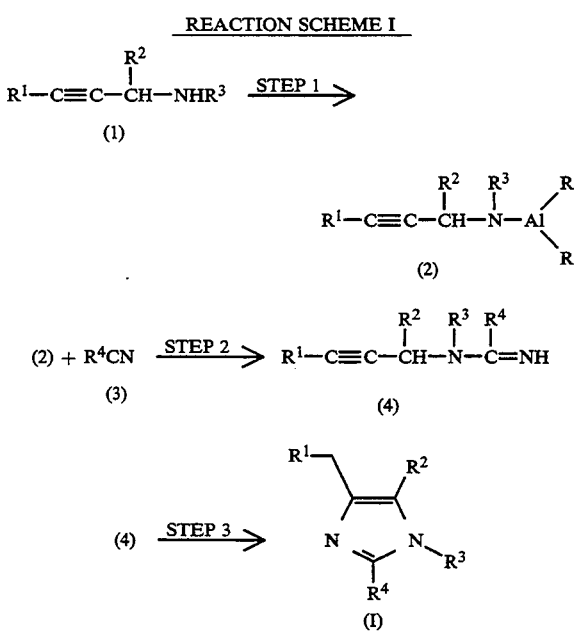

where R is lower alkyl, and $R^1$, $R^2$, $R^3$, and $R^4$ are as defined in the Summary of the Invention.

Step 1—Preparation of a compound of Formula (2)

The reaction of Step 1 in its broadest aspect comprises the reaction of a compound of Formula (1) with a tri(lower alkyl)aluminum or di(lower alkyl)-halogenoaluminum, to give a compound of Formula (2).

The compound of Formula (1) is reacted with about 1 to 1.1 molar equivalents, preferably about 1.05 molar equivalents, of a tri(lower alkyl)aluminum or di(lower alkyl)halogenoaluminum compound, preferably trimethylaluminum. The reaction is carried out in an inert solvent, preferably toluene, at a temperature of about −10° to 40° C., preferably at about 0°–25° C., for about 30 minutes to 2 hours, preferably about 1 hour. The product of Formula (2) is preferably not isolated, but used immediately in the next reaction.

Step 2—Preparation of a compound of Formula (4)

The reaction of Step 2 in its broadest aspect comprises the reaction of a compound of Formula (2) with a nitrile of formula $R^4CN$ (3), where $R^4$ is as defined in the Summary of the Invention, followed by hydrolysis, to give a compound of Formula (4).

The compound of Formula (2), prepared as shown in Step 1 above, is reacted with about 0.7 to 1.1 molar equivalents, preferably about 0.9 molar equivalents, of a nitrile of Formula (3). The reaction is carried out in an inert solvent, preferably toluene, at a temperature of about 80°–120° C., preferably at about 110° C., for about 1–6 hours, preferably about 3 hours. The reaction mixture is then cooled to a temperature of about 0°–40° C., preferably at about 5° C., and about 1–5 molar equivalents, preferably about 1.2 to 3 molar equivalents, of a protic solvent or a salt added (for example methanol, ethanol, n-propanol, sodium fluoride, preferably methanol), followed by water and filtration. The filtrate containing the product of Formula (4) is preferably used immediately in the next reaction.

It should be noted that for compounds of Formula (4) where $R^3$ is not hydrogen, the addition of a protic solvent can be omitted, as the toluene solution of the aluminum complex will cyclize directly to a compound of Formula (I) under the conditions shown below in Step 3, refluxing for a longer period of time, for example for about 6–12 hours, preferably about 8 hours.

Step 3—Preparation of a compound of Formula (I)

The reaction of Step 3 in its broadest aspect comprises the cyclization of a compound of Formula (4), to give a compound of Formula (I).

The filtrate containing the compound of Formula (4), prepared as shown in Step 2 above, is heated at a temperature of about 80°–120° C., preferably at about reflux temperature, for about 4–24 hours, preferably about 12 hours. The product of Formula (I) is isolated by conventional means, preferably by filtration.

Alternatively, the compound of Formula (4) is isolated from the filtrate by removing the solvent under reduced pressure, dissolving in an inert solvent (for example, tetrahydrofuran, ethanol or acetonitrile, preferably ethanol or acetonitrile), and heated at a temperature of about 50°–100° C., preferably at about reflux temperature, for about 4–16 hours, preferably about 8 hours The product of Formula (I) is isolated by conventional means, preferably by crystallization from the reaction medium and filtration.

Alternatively, and preferably, the compound of Formula (4) is isolated from the filtrate by removing the solvent under reduced pressure, dissolving in an inert solvent (for example, tetrahydrofuran, ethanol or acetonitrile, preferably ethanol or acetonitrile), and heated at a temperature of about 50°–100° C., preferably at about 80° C., for about 1–6 hours, preferably about 3 hours, in the presence of a palladium or gold catalyst, more preferably a palladium(II) catalyst (for example palladium(II) acetate, palladium(II) trifluoroacetate) or sodium tetrachloroaurate dihydrate, most preferably palladium-(II) acetate. The product of Formula (I) is isolated by conventional means, preferably by acid/base extraction followed by crystallization.

PROCESS FOR THE PREPARATION OF COMPOUNDS OF FORMULA (II)

The process for the preparation of compounds of Formula (II) is shown below in Reaction Scheme II:

REACTION SCHEME II

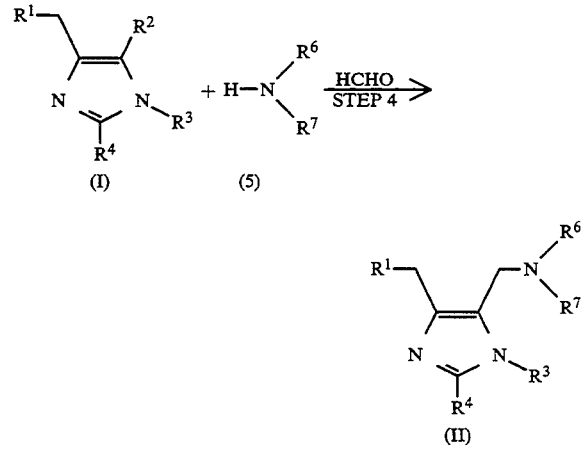

where $R^2$ is hydrogen and $R^1$, $R^3$, $R^4$, $R^6$, and $R^7$ are as defined in the Summary of the Invention.

Preparation of Starting Materials

The starting compounds of Formula (5) are commercially available, or may be prepared by means well known in the art.

Step 4—Preparation of a Compound of Formula (II)

The reaction of Step 4 in its broadest aspect comprises the reaction of a compound of Formula (I) with an amine of Formula (5) in the presence of formaldehyde, to give a compound of Formula (II).

The compound of Formula (I), prepared as shown in Step 3 above, is reacted with about 1 to 1.2 molar equivalents, preferably about 1 molar equivalent, of an amine of Formula (5), and about 2 to 10 molar equivalents, preferably about 6 molar equivalents, of formaldehyde, preferably 37% aqueous formaldehyde. The reaction is carried out in an inert solvent (for example acetone, methanol, ethanol, n-propanol, water, preferably ethanol), at a temperature of about 50°–100° C., preferably at about reflux temperature, for about 30 minutes to 6 hours, preferably about i hour. The product of Formula (II) is isolated by conventional means, preferably by conversion to an acid addition salt followed by crystallization.

Alternatively, the compound of Formula (I) is reacted with formaldehyde and an acid addition salt of an amine of Formula (5) in the proportions shown above. In this manner, the product of Formula (II) is obtained as an acid addition salt directly, which is preferably purified by crystallization.

ALTERNATIVE PROCESS FOR THE PREPARATION OF COMPOUNDS OF FORMULA (II)

Compounds of Formula (II) in which $R^3$ has three or more carbon atoms, for example n-propyl, isopropyl, isobutyl, and the like, are preferably prepared by a different process than that shown in Reaction Scheme II, because the presence of such a bulky group sterically hinders substitution at the 5-position of the starting imidazole of Formula (I). This alternative process for the preparation of compounds of Formula (II) is shown below in Reaction Scheme III:

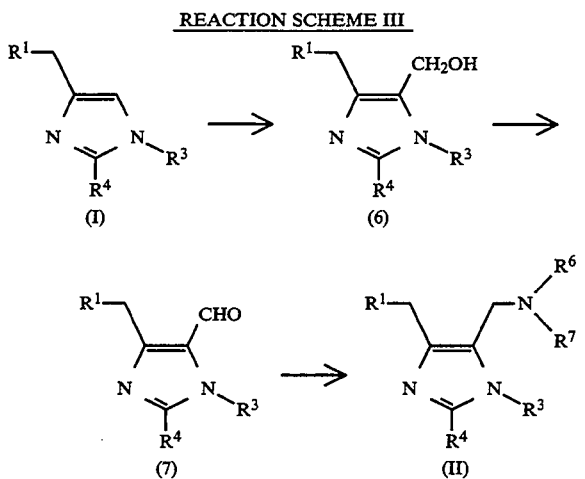

where $R^1$, $R^3$, $R^4$, $R^6$, and $R^7$ are as defined in the Summary of the Invention.

Preparation of Compounds of Formula (6)

To prepare compounds of Formula (6), an imidazole of Formula (I) is reacted with an excess of formaldehyde in the presence of an organic acid and its sodium salt, preferably acetic acid and sodium acetate, at a temperature of about 80°–140° C., preferably at about 120° C., for about 10 to 48 hours, preferably about 24 hours. When the reaction is substantially complete, the product of Formula (6) is isolated and purified by conventional means, preferably chromatography.

Preparation of Compounds of Formula (7)

To prepare compounds of Formula (7), a compound of Formula (6) is reacted with an excess of an oxidizing agent (for example, pyridine chlorochromate and the like, manganese dioxide, preferably manganese dioxide). The reaction is carried out in an inert solvent, preferably chloroform, at a temperature of about 50°–80° C., preferably at about 60° C., for about 6 to 48 hours, preferably about 24 hours. When the reaction is substantially complete, the product of Formula (7) is isolated and purified by conventional means.

Preparation of Compounds of Formula (II)

To prepare compounds of Formula (II), an amine of formula —$NR^6R^7$ is reacted with about 1 to 1.2 molar equivalents, preferably about 1.05 molar equivalents, of a compound of Formula (7) in the presence of a titanium(IV) catalyst (for example titanium ethoxide, n-propoxide, isopropoxide, n-butoxide, preferably titanium isopropoxide). The reaction is carried out in a protic solvent (for example methanol, ethanol, propanol, preferably ethanol), at a temperature of about 0°–4° C., preferably at about 25° C., for about 10 minutes to 4 hours, preferably about 1 hour. To the reaction mixture is then added a reducing agent (for example sodium borohydride and the like, sodium cyanoborohydride, preferably sodium cyanoborohydride), and the reaction continued for about 10 minutes to 4 hours, preferably about 1 hour. When the reaction is substantially complete, the product of Formula (II) is isolated and purified by conventional means, preferably flash chromatography followed by conversion to an acid salt, preferably a hydrochloride salt.

Isolation and Purification of the Compounds

Isolation and purification of the compounds and intermediates described herein can be effected, if desired, any suitable separation or purification procedure such as, for example, filtration, extraction, crystallization, column chromatography, thin-layer chromatography, thick-layer chromatography, preparative low or high-pressure liquid chromatography, distillation, or a combination of these procedures. Specific illustrations of suitable separation and isolation procedures can be had by reference to the Examples hereinbelow. However, other equivalent separation or isolation procedures could, of course, also be used.

Salts of Compounds of Formula (II)

The compounds of Formula (II) may be converted to a corresponding acid addition salt by virtue of the presence of basic nitrogen atoms. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained at 0°–50° C. The resulting salt precipitates spontaneously or may be brought out of solution with a less polar solvent.

Utility and Methods of Administration

A. General Utility

The compounds of this invention are useful for treating mammals having a variety of vascular disease states, and have protective activity against some of the deleterious effects resultant upon cerebral ischemia. Disease states that may be treated include:

diseases treated by direct neuronal protection, such as ischaemia including focal and global ischaemia, cerebral ischaemia including ischaemia-induced neurodegeneration, perinatal asphyxia, spinal injuries, peripheral nerve ischaemia, peripheral nerve damage, head trauma, primary intracerebral hemorrhage, encephalopathy, epilepsy or epileptic psychotic symptoms, and neurological diseases such as Alzheimer's, Huntington's chorea, Parkinsons and dementias; and diseases treated by calcium channel inhibition, sodium channel inhibition, or inhibition of both calcium and sodium channels, including:
 diseases treated by inhibiting cerebrovascular vasospasm and by cerebrovascular vasodilation, such as migraine, stroke, vasospasm due to subarachnoid hemorrhage, and cerebrovascular ischaemia induced by cocaine abuse;

diseases treated by inhibiting cellular oedema, such as cerebral oedema and hyponatraemic encephalopathy;

cardiovascular diseases, such as hypertension, angina, stable and unstable angina, Prinzmetal angina, arrhythmia, thrombosis, myocardial infarction, embolism, and congestive heart failure such as chronic or acute cardiac failure;

diseases characterized by ischaemia of lower legs due to peripheral vascular disease, including intermittent claudication;

diseases characterized by spasms of smooth muscle, including reversible airways obstruction, asthma, spasms of the ureter, spasms of the bladder, uterine cramps, and irritable bowel syndrome;

prevention of vasoconstriction and/or ischaemic tissue damage during a surgical procedure, such as bypass grafts, angiography, angioplasty, organ preservation during transplant, hypertensive crisis, or post-operative hypertension; and diseases treated by diuresis; and uraemic encephalopathy.

The compounds of this invention are particularly useful for treating cerebrovascular disease states, for example, stroke.

Generally, vascular disease states are found in mammals, including: domestic commercial animals such as horses, cattle, sheep and pigs; domestic house animals such as dogs, cats, and the like; and particularly humans.

B. Activity Testing

Affinity for sodium channels and interaction with sodium and calcium currents can be determined in vitro, and activity for treating cerebrovascular disease states can be determined in vivo by ascertaining the neuroprotective effect. Sodium channel affinity is determined in vitro by measuring the displacement of [$^3$H]-batrachotoxin from its binding sites on the sodium channel, as shown in Example 10.

Sodium and calcium channel activities are determined in vitro by whole cell voltage-clamp recordings of sodium and channel currents, as shown in Example 11.

In vivo activity can be determined according to the mouse model of focal ischaemia (the mouse middle cerebral artery occlusion, or "MCA" model) Gotti, B. et al., Brain Res, 1990, 522, 290–307. The MCA model entails an indirect measure of neuronal cell death following an ischemic event (i.e., occlusion of the left middle cerebral artery).

C. General Administration

The compounds of this invention are administered at a therapeutically effective dosage, i.e., a dosage sufficient to provide treatment for the disease states previously described. Administration of the active compounds and salts described herein can be via any of the accepted modes of administration for agents that serve similar utilities.

Generally, a daily dose of the active ingredient, a compound of Formula (II), is from about 0.01 to 50 mg/kg of body weight per day. Most conditions respond to treatment comprising a dosage level on the order of 0.1 to 4 mg/Kg of body weight per day. Thus, for administration to a 70 kg person, the dosage range would be about 1.4 to 3500 mg per day, preferably about 7.0 to 280 mg per day.

Depending on the specific disease state, administration can be via any accepted systemic route, for example, via parenteral, oral, intravenous, or nasal routes, in the form of solid, semi-solid or liquid dosage forms, such as for example, tablets, suppositories, capsules, powders, solutions, suspensions, aerosols, emulsions or the like, preferably in unit dosage forms suitable for simple administration of precise dosages. The compositions will include a conventional pharmaceutical carrier (or carriers) or excipient (or excipients) and an active compound of Formula II and, in addition, may include other medicinal agents, pharmaceutical agents, adjuvants, etc.

If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

The compounds of this invention are generally administered as a pharmaceutical composition which comprises a pharmaceutical excipient in combination with a compound of Formula (II). The level of the drug in a formulation can vary within the full range employed by those skilled in the art, e.g., from about 0.01 percent weight (%w) to about 99.99%w of the drug based on the total formulation and about 0.01%w to 99.99%w excipient. Preferably, the formulation will be about 3.5 to 60% by weight of the pharmaceutically active compound, with the rest being suitable pharmaceutical excipients.

Oral Administration

The preferred manner of administration, for the conditions detailed above, is oral using a convenient daily dosage regimen which can be adjusted according to the degree of affliction. For such oral administration, a pharmaceutically acceptable, non-toxic composition is formed by the incorporation of any of the normally employed excipients, such as, for example, pharmaceutical grades of mannitol, lactose, starch, magnesium stearate, sodium saccharine, talcum, cellulose, glucose, gelatin, sucrose, magnesium carbonate, and the like. Such compositions take the form of solutions, suspensions, tablets, capsules, powders, sustained release formulations and the like. Such compositions may contain between 0.01 wt/% and 99.99 wt/% of the compound of Formula II, but preferably such compositions will contain between 25 wt/% and about 80 wt/%.

Preferably the compositions will take the form of a capsule or tablet and thus the composition will contain, along with the active ingredient, a diluent such as lactose, sucrose, dicalcium phosphate, and the like; a disintegrant such as starch or derivatives thereof; a lubricant such as magnesium stearate and the like; and a binder such as a starch, polyvinylpyrrolidone, gum acacia, gelatin, cellulose and derivatives thereof, and the like.

Suppositories

For systemic administration via suppository, traditional binders and carriers include, for example, polyalkaline glycol or glycerides [e.g., PEG 1000 (96%) and PEG 4000 (4%)]. Such suppositories may be formed from mixtures containing active ingredients in the range of from about 0.5 wt/% to about 10 wt/%; preferably from about 1 wt/% to about 2 wt/%.

Liquids

Liquid pharmaceutically administrable compositions can, for example, be prepared by dissolving, dispersing, etc. an active compound (about 0.5% to about 20%), as described above, and optional pharmaceutical adjuvants in a carrier, such as, for example, water, saline, aqueous dextrose, glycerol, ethanol and the like, to thereby form a solution or suspension.

Other useful formulations include those set forth in U.S. Pat. Nos. Re. 28,819 and 4,358,603.

The formulation can be administered in a single unit dosage form for continuous treatment or in a single unit dosage form ad libitum when relief of symptoms is specifically required.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

A more recently devised approach for parenteral administration employs the implantation of a slow-release or sustained-release system, such that a constant level of dosage is maintained. See, e.g., U.S. Pat. No. 3,710,795.

The percentage of active compound contained in such parenteral compositions is highly dependent on the specific nature thereof, as well as the activity of the compound and the needs of the subject. However, percentages of active ingredient of 0.01% to 40% in solution are employable, and will be higher if the composition is a solid which will be subsequently diluted to the above percentages. Preferably the composition will comprise 0.2–10% of the active agent in solution.

Nasal administration is generally characterized by inhalation of the compounds of Formula (II) alone or in combination with other pharmaceutically acceptable excipients.

Formulations of compounds of Formula (II) may also be administered to the respiratory tract as an aerosol or solution for a nebulizer, or as a microfine powder for insufflation. In such a case, the particles of the formulation have diameters of less than 50 microns, preferably less than 10 microns.

Actual methods of preparing such dosage forms are known, or will be apparent, to those skilled in this art; for example, see *Remington's Pharmaceutical Sciences*, Mack Publishing Company, Easton, Pa., 16th Ed., 1980. The composition to be administered will, in any event, contain a quantity of the active compound(s) in a pharmaceutically effective amount for relief of the particular condition being treated in accordance with the teachings of this invention.

EXAMPLES

The following examples are given to enable those skilled in the art to more clearly understand and practice the present invention. They should not be considered as a limitation on the scope of the invention, but merely as being illustrative and representative of the preferred embodiments of the present invention.

Unless specified to the contrary, these examples are carried out under an inert atmosphere, for example nitrogen or argon.

EXAMPLE 1

Preparation of Compounds of Formula

A. Preparation of (I) where $R^1$, $R^2$ and $R^3$ are Hydrogen, and $R^4$ is 4-Methylphenyl (i) Preparation of (2) where $R^1$, $R^2$ and $R^3$ are Hydrogen To 300 ml of toluene at 0° C. was added 100 ml of trimethylaluminum (2.0M in toluene). To this solution 13.04 ml of propargylamine was added dropwise, and the reaction mixture stirred for I hour at room temperature. The product, an aluminum complex of Formula (2), was not separated, but reacted further as shown below in Part (ii).

(ii) Preparation of (4) where $R^1$, $R^2$ and $R^3$ are Hydrogen, and $R^4$ is 4-Methylphenyl To the aluminum complex of Formula (2) prepared in Part (i) above, 19.33 g of 4-toluonitrile, a compound of Formula (3), in 50 ml of toluene was added, and the mixture was refluxed for 3 hours. After cooling to room temperature, 8.1 ml of methanol was added, followed by 40 ml of water. The precipitate was removed by filtration, and the organic layer separated. The product, an amidine of Formula (4) in toluene solution, was reacted further as shown below in Part (iii).

(iii) Preparation of (I) where $R^1$, $R^2$ and $R^3$ are Hydrogen, and $R^4$ is 4-Methylphenyl The amidine of Formula (4) in toluene solution, prepared as shown in Part (ii) above, was refluxed for 11 hours. On allowing to cool to room temperature, crystals formed, which after standing for 12 hours were filtered off, giving 15.25 g (54% yield) of 4(5)-methyl-2-(4-methylphenyl)-1H-imidazole, m.p. 219° C.

B. Alternative Preparation of (I) where $R^1$, $R^2$ and $R^3$ are Hydrogen, and $R^4$ is 4-Chlorophenyl (i) Preparation of (2) where $R^1$, $R^2$ and $R^3$ are Hydrogen To 200 ml of toluene at 0° C. was added 60 ml of trimethylaluminum (2.0M in toluene). To this solution 7.65 ml of propargylamine was added dropwise, and the reaction mixture stirred for 20 minutes at 0° C., and then for 45 minutes at room temperature. The product, an aluminum complex of Formula (2), was not separated, but reacted further as shown below in Part (ii).

(ii) Preparation of (4) where $R^1$, $R^2$ and $R^3$ are Hydrogen, and $R^4$ is 4-Chlorophenyl To the aluminum complex of Formula (2) prepared in Part (i) above, 12.38 g of 4-chlorobenzonitrile, a compound of Formula (3), in 50 ml of toluene was added, and the mixture was heated at 100° C. for 5 hours. After cooling to 5° C., 20.16 g of sodium fluoride was added, followed by 7 ml of water, and the mixture stirred at 5° C. for 20 minutes. The precipitate was removed by filtration through diatomaceous earth. Solvent was removed from the filtrate under reduced pressure, and the residue, an amidine of Formula (4), was reacted further as shown below in Part (iii).

(iii) Preparation of (I) where $R^1$, $R^2$ and $R^3$ are Hydrogen, and $R^4$ is 4-Chlorophenyl The amidine of Formula (4) was dissolved in 350 ml of acetonitrile, and palladium(II) acetate (930 mg) added. The solution was refluxed for 2⅔ hours, then solvent removed under reduced pressure. The residue was dissolved in 250 ml of 10% hydrochloric acid, and washed twice with 150 ml of dichloromethane. Concentrated sodium hydroxide solution was then added to the aqueous phase until a pH of 10 was attained, and the mixture extracted with dichloromethane. The organic layer was dried over sodium sulfate, and solvent removed to yield a solid, which was recrystallized from dichloromethane/ether mixture to give 9.49 g of 4(5)-methyl-2-(4-chlorophenyl)-1H-imidazole, m.p. 234°–235° C.

C. Preparation of (I), varying $R^1$, $R^2$, $R^3$ and $R^4$

Similarly, following the procedures of Example 1A or 1B, Parts (i), (ii) and (iii) above, but in Step (i) replacing propargylamine with:

N-methylpropargylamine;
N-propylpropargylamine;
N-(isopropyl)propargylamine;
N-(n-butyl)propargylamine;
N-(isobutyl)propargylamine;
1-(methylamino)hex-2-yne;

and in Step (ii) replacing 4-toluonitrile with:

4-methoxybenzonitrile;
4-trifluoromethylbenzonitrile;
4-nitrobenzonitrile;
4-fluorobenzonitrile;
n-butyl cyanide;
valeronitrile;
isovaleronitrile;
benzylthiocyanate;
methyl thiocyanate; and
3,4-dimethoxybenzonitrile;

the following compounds of Formula (I) were prepared:

4(5)-methyl-2-(4-trifluoromethylphenyl)-1H-imidazole, m.p. 250° C. (decomp);
4(5)-methyl-2-(4-methoxyphenyl)-1H-imidazole, m.p. 215°–216° C.;
4(5)-methyl-2-(4-fluorophenyl)-1H-imidazole, m.p. 186° C.;
4(5)-methyl-2-(4-nitrophenyl)-1H-imidazole m.p. >260° C.;
1,4-dimethyl-2-(4-trifluoromethylphenyl)imidazole, m.p. 65°–66° C.;
1,4-dimethyl-2-(4-nitrophenyl)imidazole, m.p. 70°–71° C.;
4-methyl-1-(2-methylprop-1-yl)-2-(4-trifluoromethylphenyl)imidazole, m.p. 68° C.;
4(5)-methyl-2-(2-methylprop-1-yl)-1H-imidazole, m.p. 70° C.;
4-methyl-1-(1-methyleth-1-yl)-2-(4-trifluoromethylphenyl)imidazole, oil;
1-(n-butyl)-4-methyl-2-(4-trifluoromethylphenyl)imidazole, oil;
1,4-dimethyl-2-(n-butyl)imidazole, m.p. oil;
1,4-dimethyl-2-(benzylthio)imidazole, m.p. oil;
1,4-dimethyl-2-(methylthio)imidazole, m.p. oil;
1,4-dimethyl-2-(3,4-dimethoxyphenyl)imidazole, m.p. 120°–121° C.;
1-methyl-2-(2-methylprop-1-yl)-4-methylimidazole, oil; and
4(5)-n-propyl-2-(4-trifluoromethylphenyl)-1H-imidazole, oil.

D. Preparation of (I) varying $R^1$, $R^2$, $R^3$ and $R^4$

Similarly, following the procedures of Example 1A, Parts (i), (ii) and (iii) above, but in Step (i) optionally replacing propargylamine with other compounds of Formula (1), and in Step (ii) optionally replacing 4-toluonitrile with other compounds of Formula (3), the following compounds of Formula (I) are prepared:

4,5-dimethyl-2-(4-trifluoromethylphenyl)-1H-imidazole;
4-ethyl-2-(4-trifluoromethylphenyl)-1H-imidazole;
1,4,5-trimethyl-2-(4-trifluoromethylphenyl)imidazole;
2-(n-butyl)-4-methyl-1-(1H-tetrazol-5-yl)biphenylimidazole;
5-(n-butyl)-1-(1H-tetrazol-5-yl)biphenylimidazole; and
4-methyl-2-thiomethyl-1H-imidazole.

EXAMPLE 2

Preparation of Compounds of Formula (II)

A. Preparation of (II) where n is 0, $R^1$ and $R^3$ are Hydrogen, $R^4$ is 4-Trifluoromethylphenyl, and —$NR^6R^7$ represents 1-(Diphenylmethyl)piperazine To 300 ml of ethanol was added 13.7 g of 4(5)-methyl-2-(4-trifluoromethylphenyl)-1H-imidazole, 15.3 g of N-(diphenylmethyl)piperazine, and 30 ml of 37% aqueous formaldehyde. The mixture was refluxed for 1 hour, then cooled to room temperature. A solid precipitated out, which was filtered off and dried, to give 23.7 g (80%) of 1-diphenylmethyl-4-[(2-(4-trifluoromethylphenyl)-4-methyl-1H-imidazol-5-yl)methyl]piperazine, m.p. 244° C.

B. Preparation of (II), varying n, $R^1$, $R^3$, $R^4$, and —$NR^6R^7$

Similarly, following the procedures of Example 2A, but optionally replacing 4(5)-methyl-2-(4-trifluoromethylphenyl)-1H-imidazole with other compounds of Formula (I), and optionally replacing N-(diphenylmethyl)piperazine with other compounds of Formula (5), the following compounds of Formula (II) were prepared:

1-diphenylmethyl-4-[(2-(4-methylphenyl)-4-methyl-1H-imidazol-5-yl)methyl]piperazine, m.p. 194°–196° C.;
1-diphenylmethyl-4-[(2-(4-trifluoromethylphenyl)-4-methyl-1H-imidazol-5-yl)methyl]piperazine, m.p. of the trihydrochloride 215° C.;
1-(4-methoxyphenyl)methyl-4-[(2-(4-trifluoromethylphenyl)-4-methyl-1H-imidazol-5-yl)methyl]piperazine, m.p. 210° C.;
1-(2,3,4-trimethoxyphenyl)methyl-4-[(2-(4-trifluoromethylphenyl)-1,4-dimethylimidazol-5-yl)methyl]piperazine, m.p. of the trihydrochloride 210°–215° C.;
1-(3,4-dimethoxyphenyl)methyl-4-[(2-(4-trifluoromethylphenyl)-4-methyl-1H-imidazol-5-yl)methyl]piperazine, m.p. of the trihydrochloride 222° C.;
1-(2,3-dimethoxyphenyl)methyl-4-[(2-(4-trifluoromethylphenyl)-4-methyl-1H-imidazol-5-yl)methyl]piperazine, m.p. of the trihydrochloride 220° C.;
1-(2,3,4-trimethoxyphenyl)methyl-4-[(2-(4-fluorophenyl)-4-methyl-1H-imidazol-5-yl)methyl]piperazine, m.p. 160° C.;
1-(2,3,4-trimethoxyphenyl)methyl-4-[(2-(4-chlorophenyl)-4-methyl-1H-imidazol-5-yl)methyl]piperazine, m.p. of the trihydrochloride 182°–185° C.;
1-(2,3,4-trimethoxyphenyl)methyl-4-[(2-(4-methoxyphenyl)-4-methyl-1H-imidazol-5-yl) methyl]piperazine, m.p. of the trihydrochloride 215° C.;
1-(2,3,4-trimethoxyphenyl)methyl-4-[(2-(3,4-dimethoxyphenyl)-1,4-dimethylimidazol-5-yl)methyl]- piperazine, m.p. of the trihydrochloride 192°–193° C.;

1-(2,3,4-trimethoxyphenyl)methyl-4-[(2-(4-trifluoromethylphenyl)-4-methyl-1H-imidazol-5-yl)methyl]piperazine, m.p. 152° C.; and 1-(3,4,5-trimethoxyphenyl)methyl-4-[(2-(4-trifluoromethylphenyl)-4-methyl-1H-imidazol-5-yl)methyl]piperazine, m.p. 135° C.

C. Preparation of (II), varying n, $R^1$, $R^3$, $R^4$, and $-NR^6R^7$

Similarly, following the procedures of Example 2A, but optionally replacing 4(5)-methyl-2-(4-trifluoromethyl-phenyl)-1H-imidazole with other compounds of Formula (I), and optionally replacing N-(diphenylmethyl)-piperazine with other compounds of Formula (5), the following compounds of Formula (II) are prepared:

1-diphenylmethyl-4-[(2-(4-trifluoromethylphenyl)-4-ethyl-1H-imidazol-5-yl)methyl]piperazine;

1-(2,3,4-trimethoxyphenyl)methyl-4-[(2-(4-trifluoromethylphenyl)-4-ethyl-1H-imidazol-5-yl)methyl]piperazine;

1-diphenylmethyl-4-[(2-(4-trifluoromethylphenyl)-4-methyl-1-ethylimidazol-5-yl)methyl]piperazine;

1-(2,3,4-trimethoxyphenyl)methyl-4-[(2-(4-trifluoromethylphenyl)-4-methyl-1-ethylimidazol-5-yl)methyl]piperazine;

5-(N-phenylmethyl)aminomethyl-2-(4-trifluoromethylphenyl)-1,4-dimethylimidazole;

4-diphenylmethyl-1-[(2-(4-trifluoromethylphenyl)-4-methyl-1H-imidazol-5-yl)methyl]piperidine; and 1-diphenylmethyl-4-[(2-phenyl-4-methyl-1H-imidazol-5-yl)methyl]piperazine.

EXAMPLE 3

Alternative Preparation of Compounds of Formula (II)

A. Preparation of (II) where n is 0, $R^1$ is Hydrogen, $R^3$ is Isobutyl, $R^4$ is 4-Trifluoromethylphenyl, and $-NR^6R^7$ represents 1-(Diphenylmethyl)piperazine A solution of 1-isobutyl-2-(4-trifluoromethylphenyl)-4-methyl-5-formylimidazole (1.6 g), N-(diphenylmethyl)piperazine (1.3 g), and titanium tetraisopropoxide (2 ml) were stirred for 1 hour at room temperature. Ethanol (10 ml) was added, and the resultant solution was stirred for a further 30 minutes. Sodium cyanoborohydride (330 mg) was then added, and the mixture stirred overnight. The solvent was removed under reduced pressure, and the residue partitioned between methylene chloride/water. The organic phase was separated, dried over anhydrous magnesium sulfate, filtered and evaporated. The residue was flash-chromatographed on silica gel, eluting with ethyl acetate/n-heptane (1/2), to yield 1.0 g of 1-diphenylmethyl-4-[(1-isobutyl-2-(4-trifluoromethylphenyl)-4-methylimidazol-5-yl)methyl]piperazine. Treatment with anhydrous hydrochloric acid in ethanol converted the base to its trihydrochloride salt, m.p. 200° C.

B. Preparation of (II), varying $R^1$, $R^3$, $R^4$, and $-NR^6R^7$

Similarly, following the procedures of Example 3A, but optionally replacing 1-isobutyl-2-(4-trifluoromethylphenyl)-4-methyl-5-formylimidazole with other compounds of Formula (I), and optionally replacing N-(diphenylmethyl)piperazine with other compounds of Formula (5), the following compounds of Formula (II) were prepared:

1-(2,3,4-trimethoxyphenyl) methyl-4-[(1,4-dimethyl-2-(4-nitrophenyl)imidazol-5-yl) methyl]piperazine, m.p. of the trihydrochloride 180 ° C.;

1-diphenylmethyl-4-[(1-(n-propyl)-2-(4-trifluoromethylphenyl)-4-methylimidazol-5-yl)methyl]piperazine, m.p. of the trihydrochloride 185° C.;

1-diphenylmethyl-4-[(1-(isopropyl)-2-(4-trifluoromethylphenyl)-4-methylimidazol-5-yl) methyl]piperazine, m.p. of the trihydrochloride 190° C.;

1-(2,3,4-trimethoxyphenyl)methyl-4-[(1-(n-butyl-2-(4-nitrophenyl)-4-methylimidazol-5-yl)methyl]piperazine, m.p. of the trihydrochloride 180° C.; and 1-diphenylmethyl-4-[(1-(n-butyl)-2-(4-trifluoromethylphenyl)-4-methylimidazol-5-yl)methyl]piperazine, m.p. of the trihydrochloride 200° C.

EXAMPLES 4–8

The following examples illustrate the preparation of representative pharmaceutical formulations containing a compound of Formula (II), e.g., 1-diphenylmethyl-4-[(2-(4-trifluoromethylphenyl)-4-methyl-1H-imidazol-5-yl)methyl]piperazine. Other compounds and salts of Formula (II), such as those prepared in accordance with Example 2, can be used as the active compound in the formulations of Examples 3–7.

EXAMPLE 4

| I.V. Formulation | |
|---|---|
| Active compound | 0.60 g |
| Tartaric acid | 0.618 g |
| Sorbitol | 4.05 g |
| Water | to 100 ml |

Other compounds of Formula II and the pharmaceutically acceptable salts thereof may be substituted therein.

EXAMPLE 5

| Ingredients | Quantity per tablet, mgs. |
|---|---|
| Active compound | 25 |
| cornstarch | 20 |
| lactose, spray-dried | 153 |
| magnesium stearate | 2 |

The above ingredients are thoroughly mixed and pressed into single scored tablets.

EXAMPLE 6

| Ingredients | Quantity per capsule, mgs. |
|---|---|
| Active compound | 100 |
| lactose, spray-dried | 148 |
| magnesium stearate | 2 |

The above ingredients are mixed and introduced into a hard-shell gelatin capsule.

EXAMPLE 7

| Ingredients | Quantity per tablet, mgs. |
|---|---|
| Active compound | 1 |
| cornstarch | 50 |
| lactose | 145 |
| magnesium stearate | 5 |

The above ingredients are mixed intimately and pressed into single scored tablets.

EXAMPLE 8

| Ingredients | Quantity per capsule, mgs. |
| --- | --- |
| Active compound | 150 |
| lactose | 92 |

The above ingredients are mixed and introduced into a hard-shell gelatin capsule.

EXAMPLE 9

Determination of Activity Utilizing The MCA Model

Adult male mice ($CD_1$ strain), weighing 30–40 g, were anaesthetized by 5% halothane in a 70%:30% nitrous oxide:oxygen gas mixture.

The left middle cerebral artery was exposed through a curved incision midway between the eye and the external auditory meatus, the artery was sealed by thermocautery.

The dosing schedule was as follows. The first dose of test compound (0.01–0.5 mg/kg intraperitoneally) was administered 15 minutes following ischaemia. The mice then recovered for seven days, during which time they were dosed with the same amount of test compound twice daily at approximately 9 am and 4 pm.

The animals were sacrificed 4 h after the last dose. The infarcted area was dissected from the ischemic left hemisphere and the contralateral right hemispherical area was also taken as control non-ischemic tissue.

Damage in the ischemic hemisphere was quantified by measuring the binding of [$^3$H]-PK 11195, which provides an index of ischemic damage insofar as an increase in binding of [$^3$H]-PK 11195 (assessed by $B_{max}$) indirectly reflects neuronal damage. Compounds which prevent the increase in the number of binding sites are considered to be neuroprotective.

Animals treated with placebo showed an increase in the $B_{max}$ of [$^3$H]-PK 11195 binding in the ischemic hemisphere resulting in an increase in the ratio of binding of the left (ischemic) hemisphere:right (non-ischemic) hemisphere. This was taken as 100% damage against which the effect of test compounds could be calculated.

There were no changes in the affinity of [$^3$H]-PK 11195 for its binding sites in the study.

The compounds of Formula (II) show neuroprotective effects in this model.

This procedure is a modification of a procedure initially described by Gotti, B. et al, *Brain Res.*, (1990), Vol. 522, 290–307.

EXAMPLE 10

Determination of Na+ Channel Binding Site Affinity ([$^3$H]-batrachotoxin)

Washed rat brain synaptosomal homogenates are incubated with [$^3$H]-batrachotoxin ([$^3$H]-BTX, 5nM) with and without the test compound over a concentration range of $10^{-10}$–$10^{-4}$M in Hepes buffer (163 mM choline, 5 mM Hepes, 1.8 mM $CaCl_2$, 0.8 mM $MgSO_4$, 0.1 mg/ml BSA, pH 7.4) containing tetrodotoxin (final assay concentration 7 $\mu$M) and scorpion toxin (final assay concentration 1 $\mu$M) in a final volume of 350 $\mu$l. Non-specific binding is defined using a saturating concentration of veratridine (0.3 mM). The assay tubes are incubated at 37° C. for 30 min then filtered over Whatman GF/B glass fibre filtermats using a Brandel cell harvester. Bound radioactivity is assessed by liquid scintillation spectrometry. The affinity of the test compounds for the Na+ channel were compared as $pIC_{50}$ values.

The compounds of Formula (II) show a high affinity for the sodium channel.

EXAMPLE 11

Whole cell voltage clamp recordings of Sodium currents ($I_{Na}$) from N1E 115 Deuroblastoma cells This is a whole cell variant of the patch clamp technique (Hammill et al., Pflugers Arch. (1981) 391, 85–100).

The ionic composition of the internal solution was (in mM): 120 CsF, 10 NaCl, 11 EGTA, 10 HEPES, 10 tetraethylammonium Cl, 1 $CaCl_2$, 1 $MgCl_2$ (pH to 7.3 with CsOH) and the external solution contained 145 NaCl, 3 KCl, 10 HEPES, 1 $CaCl_2$, 1 $MgCl_2$, 0.5 $CdCl_2$, 5 glucose (pH to 7.3 with NaOH).

Cells were held at a membrane potential of −80mV and $I_{Na}$ was evoked by 10 ms depolarizing steps to OmV until a stable current was recorded. A current-/voltage curve was then constructed by applying a series of depolarizing steps to membrane potentials ranging from −60 to +70 mV (increments of 10 mV). Test compounds were then applied at 3 $\mu$M or 10 $\mu$M for 10 minutes after which a second current/voltage curve was recorded.

When tested in this way, the compounds of Formula (II) produce an inhibition of the peak inward sodium current ($I_{Na}$) (measured from the current/voltage curve).

EXAMPLE 12

Whole cell voltage clamp recordings of T-type Calcium currents ($I_{Ca(T)}$)

This is a whole cell variant of the patch clamp technique (Hammill et al., Pflugers Arch. (1981) 391, 85–100).

The ionic composition of the internal solution was (in mM): 120 CsCl, 10 NaCl, 11 EGTA, 10 HEPES, 10 tetraethylammonium Cl, 1 $CaCl_2$, 1 $MgCl_2$, 40 sucrose (pH adjusted to 7.4 with CsOH) and the external solution contained 110 Tris base, 20 $BaCl_2$, 5 CsCl, 5 KCl, 20 HEPES, 30 Glucose (pH adjusted to 7.4 with HCl).

Cells were clamped at a membrane potential of −80 mV and $I_{Ca(T)}$ was evoked by 150 ms depolarizing steps to −10 mV until a stable current was elicited. A current/voltage curve was then constructed by applying a series of depolarizing steps to membrane potentials ranging from −60 to +40 mV (in increments of 10 mV). A test compound was then introduced into the superfusing medium to give a final concentration of 1 $\mu$M or 3 $\mu$M. Drug was applied for 10 minutes after which a second current/voltage curve was recorded.

When tested in this way, the compounds of Formula (II) significantly inhibit T-type calcium currents.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What we claim is:

1. A process for the preparation of compounds represented by the formula:

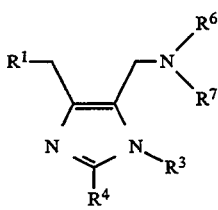

wherein:
$R^1$ is hydrogen or lower alkyl;
$R^3$ is hydrogen or alkyl;
$R^4$ is lower alkyl or optionally substituted phenyl;
$R^6$ is hydrogen or lower alkyl;
$R^7$ is

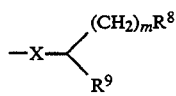

or $R^6$ and $R^7$ taken together with the nitrogen atom to which they are attached represent a group of the formula:

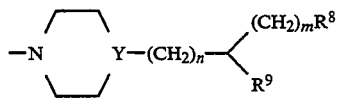

wherein:
m is 0 or 1;
n is 0, 1, 2 or 3;
$R^8$ is hydrogen, lower alkyl, or optionally substituted phenyl;
$R^9$ is optionally substituted phenyl;
X is —$(CH_2)_n$—, or 1-piperidin-4-yl; and
Y is —CH—, or —N—;
which process comprises:
a) cyclizing a compound represented by the formula:

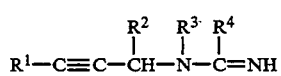

to give a compound represented by the formula:

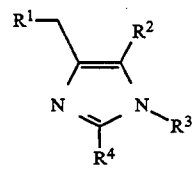

wherein $R^2$ is hydrogen and $R^1$, $R^3$ and $R^4$ are as defined; followed by:
b) contacting the compound thus formed with a compound represented by the formula:

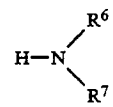

$R^6$ and $R^7$ are as defined:
in the presence of formaldehyde.

2. The process of claim 1, wherein in step a) the cyclization is carried out in the presence of a catalyst chosen from palladium(II) acetate, palladium(II) trifluoroacetate, and sodium tetrachloroaurate dihydrate.

3. The process of claim 1, wherein the catalyst is palladium(II) acetate.

4. The process of claim 1, wherein the cyclization is carried out in tetrahydrofuran, ethanol or acetonitrile at reflux temperature.

5. The process of claim 1, wherein in step b) the reaction is carried out in ethanol at reflux temperature.

6. The process of claim 1, wherein $R^1$ is hydrogen, and $R^6$ and $R^7$ taken together with the nitrogen atom to which they are attached represent a group of the formula:

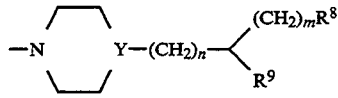

wherein m and n are both 0, and Y is —N—.

7. The process of claim 6, wherein $R^3$ is hydrogen, $R^4$ is 4-methylphenyl, and $R^8$ and $R^9$ are both phenyl.

8. The process of claim 7, wherein $R^3$ is hydrogen, $R^4$ is 4-trifluoromethylphenyl, $R^8$ is hydrogen, and $R^9$ is 2,3,4-trimethoxyphenyl.

9. The process of claim 7, wherein $R^3$ is methyl, $R^4$ is 4-trifluoromethylphenyl, and $R^8$ and $R^9$ are both phenyl.

10. The process of claim 7, wherein $R^3$ is methyl, $R^4$ is 4-trifluoromethylphenyl, $R^8$ is hydrogen, and $R^9$ is 2,3,4-trimethoxyphenyl.

* * * * *